US00PP20051P2

(12) United States Plant Patent
Walker

(10) Patent No.: US PP20,051 P2
(45) Date of Patent: Jun. 2, 2009

(54) NEMATODE RESISTANT GRAPE ROOTSTOCK '9365-43'

(50) Latin Name: *Vitis rufotomentosa×V.champinii 'Dog Ridge'×V.riparia 'Riparia Gloire'×v.champinii 'c9038'*
Varietal Denomination: 9365-43

(75) Inventor: Andrew Walker, Woodland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/009,137

(22) Filed: Jan. 15, 2008

(51) Int. Cl.
*A01H 5/00* (2006.01)

(52) U.S. Cl. ..... Plt./205
(58) Field of Classification Search ..... Plt./174, Plt./205
See application file for complete search history.

*Primary Examiner*—Annette H Para
(74) *Attorney, Agent, or Firm*—Morrison & Foerster LLP

(57) ABSTRACT

Rootstock '9365-43' is a cross of 'L514-10' (*Vitis rufotomentosa*×(*V. champinii* 'Dog Ridge'×*V. riparia* 'Riparia Gloire'))×*V. champinii* 'c9038'. The rootstock is a new and distinct variety of grape rootstock with resistance to a broad array of soil-borne nematodes including root-knot, dagger, lesion and citrus nematodes. The rootstock is susceptible to ring nematode, but has strong resistance to grape phylloxera.

2 Drawing Sheets

Botanical/commercial classification: 'L514-10' (*Vitis rufotomentosa*×(*V. champinii* 'Dog Ridge'×*V. riparia* 'Riparia Gloire'))×*V. champinii* 'c9038'.
Variety denomination: '9365-43'.

BACKGROUND OF THE INVENTION

Nematodes are important pests in vineyards around the world, and these soil-borne pests can be particularly problematic in California vineyards. Two factors intensify the impact of nematodes—the high value of grapes and of vineyard land. These factors force growers to ignore the steps of leaving land fallow and rotating crops, both of which reduce nematode build up and delay the selection of adapted strains. Nematicides and fumigants help control nematodes, but the use of these pesticides has been greatly restricted and their future use in doubt because they must be persistent and penetrate deeply through the soil profile to be highly effective. In addition, grape rootstocks were bred to resist grape phylloxera (a devastating root-feeding aphid), and were not selected for nematode resistance. The grape rootstocks 'Freedom' and 'Harmony' were released by the USDA/Fresno to provide resistance to nematodes, but they are not resistant to grape phylloxera. More recently, McKenry at UC Riverside released two rootstocks, 'RS3' and 'RS9' (siblings of a 'Schwarzmann'×'Ramsey' cross), designed to resist multiple nematode species and provide growers with nematode resistant rootstock alternatives. However, they have nematode resistance from a relatively narrow genetic base, which may promote thc evolution of strains capable of feeding on them. Therefore, there is a need to develop nematode resistant grape rootstock.

SUMMARY OF THE INVENTION

This invention relates to a new and distinct variety of grape rootstock with resistance to a broad array of soil-borne nematodes including root-knot, dagger, lesion and citrus nematodes. The variety is susceptible to ring nematode, but has strong resistance to grape phylloxera. The variety is a cross of 'L514-10' (*Vitis rufotomentosa*×(*V. champinii* 'Dog Ridge'×*V. riparia* 'Riparia Gloire'))×*V. champinii* 'c9038'. The variety is recommended for vineyard sites with severe nematode infestations.

DETAILED DESCRIPTION OF THE INVENTION

Figure 1:
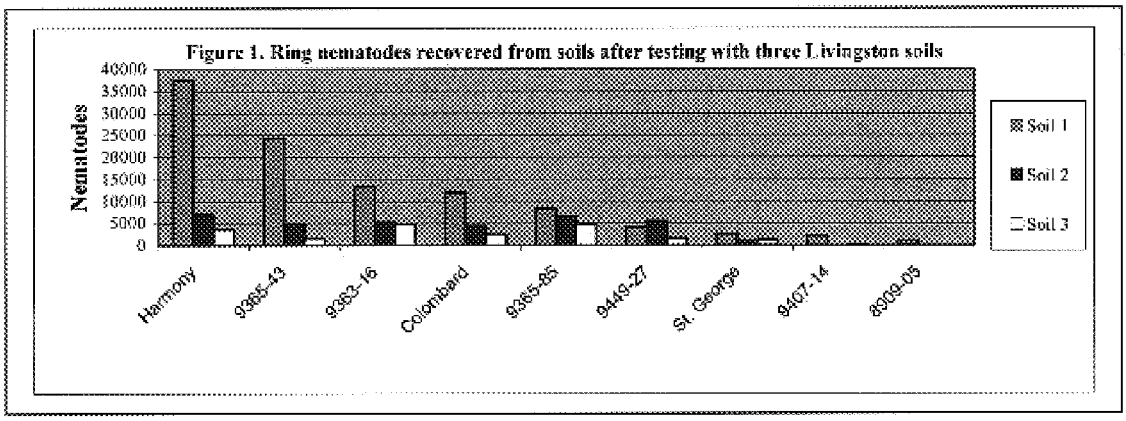
FIG. 1: number of ring nematodes recovered off rootstock selections growing in 1 gal pots with three soils collected from the Gallo Livingston Ranch, known to have severe and chronic nematode pressure. Results per soils are means of three replicate pots.
Figure 2:
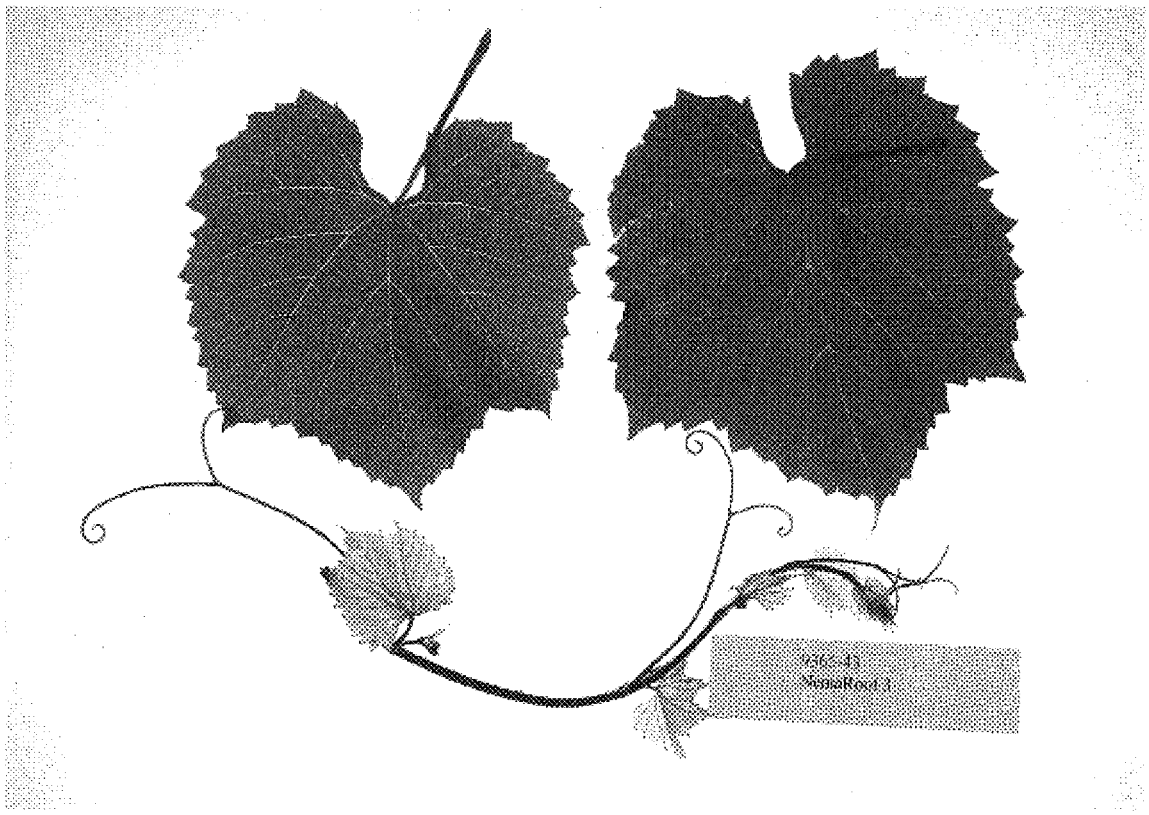
FIG. 2: a photograph showing rootstock '9365-43'.

A breeding program was initiated in 1990 at UC Davis to provide a group of rootstocks with broad and durable resistance to the nematodes found in California vineyards. This program commenced with an evaluation of selections that remained from breeding efforts in the late 1960s and early 1970s. These selections from the late 1960s and early 1970s were previously screened against two root knot nematode species (*Meloidogyne incognita acrita* and *M. arenaria thamsei*), the lesion nematode (*Pratylenchus vulnus*), and the dagger nematode (*Xiphinema index*). In 1990, these selections were evaluated for their ability to root and for growth habits such as brushy growth, internode length and the degree of lateral shoot production. In 1993 and 1994, the best of these selections were crossed to species chosen for their ability to reduce scion vigor or improve the rooting of the progeny. The parentage and species composition of '9363-16' and other crosses are listed in Table 1. About 5,000 progeny were planted in the vineyard and their evaluation for nematode resistance was initiated in 1996.

The first phase of the selection process examined the progeny for their general vigor and horticultural characters such as internode length and the degree of lateral shoot formation. The best 1,000 progeny, selected from a large number of, were advanced to a rooting assay. Ten 2-node dormant cuttings of the best 1,000 were taken in December 1996 and tested for their ability to form roots. Rootstocks that root well generally graft well, thus this evaluation was a key indicator of their future success as rootstocks. One hundred of the progeny were selected, again with an effort to get a broad representation from the large number of families.

The second phase of the selection process involved testing these 100 selections for resistance to *M. incognita* 13. This root-knot nematode isolate is capable of feeding on many rootstocks, but does not feed on rootstocks that derive their resistance from *V. champinii* ('Freedom', 'Harmony', 'Dog Ridge' and 'Ramsey'). All of the nematode testing in this breeding program utilized potted plants under greenhouse conditions with optimized soils and irrigation techniques to promote nematode feeding. Resistance to this isolate of root-knot nematode was evaluated by assaying the number of galls on the roots after inoculation with 1,000 J2 larvae (the free-living infectious stage of this nematode). Resistance was also evaluated by extracting the J2 nematodes in the pots after the root galls were counted. Later phases of the root-knot nematode screening evaluated resistance by counting the number of egg masses formed using a technique developed in the Walker lab (Cousins and Walker 2001 Plant Disease 85:1052–1054). There were no root galls on 33 of the 100 selections and the 33 selections were advanced to the next phase of screening.

The third phase of the selection process tested the 33 root-knot nematode resistant selections against two aggressive strains of root-knot nematode and against the dagger nematode, *X. index.* The two aggressive strains were selected in the Walker lab from soils provided by McKenry, from a declining 'Harmony' vineyard. Root-knot nematodes were extracted from this soil and the larvae were placed onto tomato plants with high susceptibility to root-knot nematodes. Two egg masses were collected from these infested plants and J2 larvae from each mass were put on a separate uninfested tomato plant to create new strains from a single egg mass (root-knot nematodes are parthenogenic). These new strains were multiplied on tomato and were then used to inoculate potted plants of 'Harmony' rootstock to verify their ability to feed aggressively on this resistant rootstock. These two strains were named 'HarmA' and 'HarmC'. Later investigations determined that 'HarmA' was a strain of *M. arenaria* while 'HarmC' was a strain of *M. incognita.* The dagger nematodes were collected from several vineyards in the Napa Valley of California, which were known to have fanleaf degeneration.

The 33 selections were then inoculated with each of the three nematode strains independently. The root-knot nematode screens used 1,000 J2 larvae to inoculate plants growing in 1,000 $cm^3$ plastic pots with a coarse sand/clay loam soil mix. The dagger nematode screens were done in the same pots and soils, but used 200 adult *X. index* as the inoculum. Fourteen selections did not produce egg masses when inoculated with the three root-knot nematode strains nor did they produce root tip galls after inoculation with *X. index* (Table 2).

In the fourth phase, the 14 selections were subjected to a series of tests. The first was a combined inoculum of all four nematodes at once to determine the impact of simultaneous nematode feeding on resistance (Table 3). They were also tested against the four nematodes over a range of temperatures, 24, 27, 30 and 32° C. There was some erosion of resistance to 'HarmA' (the most aggressive strain of root-knot nematode) at this temperature, but 6 of the selections performed very well (Table 4). Root-knot nematode resistance is known to fail at about 28° C. in a wide range of species including tomato, pepper and plum. The 14 selections were also evaluated for resistance to lesion (*Pratylenchus vulnus*), citrus (*Tylenchulus semipenetrans*) and ring (*Mesocriconema xenoplax*) nematodes (Table 3). From this series of tests a number of six rootstock selections were made, including '9365-43'. A summary of the characteristics of variety '9365-43' is presented below.

Grape phylloxera are capable of feeding and producing galls (nodosities) on the young roots of virtually all grape rootstocks and species. In order to gauge the phylloxera hosting ability of the final six selections, they were tested for the ability to support phylloxera on nodosities and compared to a set of commercial rootstocks. Three sets of young root pieces from each selection were inoculated with 10 phylloxera eggs collected from '101-14 Mgt' rootstock roots. Over a 21-day period, the number of eggs and juveniles that were produced were summed and divided by 10 (the original inoculum) to produce the average rate of increase. Table 5 presents these results for the six selections. Nodosity galling on young roots does not appear to damage grapevines, only feeding and galling on mature roots (tuberosities) leads to vine death. The high rate of phylloxera feeding, galling and reproduction on '101-14 Mgt' (7.98 average rate of increase) has been observed in past tests. Most of the values were very low, although this '101-14 Mgt' strain is well adapted to '9407-14'. Three of the selections were very resistant: '8909--05', '9363-16' and '9449-27'. The low values for 'AXR#1' demonstrate that the results of this test do not reflect field level or tuberosity level feeding and damage, and that phylloxera adapt independently to rootstock hosts.

It will take years to determine which sites each of these rootstock selections are best suited to, but they have unparalleled levels of resistance to nematodes and should excel in sites with single and mixed nematode species infestations. Four of the selections ('9365-43', '9365-85', '9407-14' and '9449-27') were grafted to 'Fiesta Seedless' and planted in a Fresno rootstock trial in 2004. That year two of these selections ('9365-43' and '9365-85') were also included in a Chardonnay rootstock trial in Santa Maria. The six rootstock selections in large pots using soils from the Gallo Livingston Ranch where nematode pressure from root-knot, lesion, ring and *Xiphinema americanum,* is known to be severe and chronic. This test was conducted to evaluate these selections under "field conditions" using infested soil without added inoculations. All of the selections performed very well against root-knot nematodes (Table 6) and two, '9407-14' and '8909-05', also performed very well against ring nematode (FIG. 1).

DETAILED BOTANICAL DESCRIPTION

Rootstock '9365-43' is a pistillate flowered vine with leaves that appear *V. champinii*-like with shorter teeth, thicker texture and limited lobing. It produces mothervines with moderate vigor, long straight canes with moderately long internodes and a moderate number of lateral shoots. '9365-43' had excellent nematode resistance in the combined testing, resists citrus and lesion nematodes, and is moderately susceptible to ring nematodes (Table 3). Preliminary propagation tests found it to have moderately deep rooting angles.

The following is a detailed description of rootstock '9365-43'. All color descriptions are from the Munsell Color Chart for Plant Tissues with Hue Value/Chroma values. Measurements are averages from 5 mid cane leaves and presented as length of the main vein from the petiole to the end of the apical lobe x the width from lateral lobe to lateral lobe. Grape flowers are inconspicuous and never used to distinguish varieties or species except in the case of being staminate, pistillate or hermaphroditic. The size of the young leaves is strongly influenced by the environment and was not reported.

Shoot tips—The variety has shoot tips which are enclosed in expanding leaves, green (7.5GY 4/4) and sparsely covered with arachnose tomentum.

Young leaves—The variety has young leaves which are green (7.5GY 4/4), three lobed glabrous leaves with fine arachnose tomentum and relatively long sharply pointed teeth.

Mature leaves—The variety has mature leaves which are light green upper (7.5GY 4/4) and lower (7.5GY 5/4) surfaces, medium large (10.6×13.7 cm), broadly cuneiform to orbicular shaped leaves, with short broad angular teeth and medium-sized petioles. The upper surface is glabrous, rugose and mostly flat with some puckering near the petiolar attachment. The lower surface has scattered arachnose tomentum, fine bristles along the main vines and small tufted bristles (domatia) at the intersection of the main veins. The petiolar sinus is narrow U-shape.

Canes—The variety has brown (2.5YR 5/8) canes with long internodes and limited lateral development, nodes have mediums sized rounded buds. Canes are mostly round in cross-section and have relatively thick diaphragms and medium pith.

Flowers—The flowers are pistillate with small clusters and small black berries.

TABLE 1

Parentage of the five nematode resistant grape rootstock selections.

| Selection | Parentage |
|---|---|
| '8909-05' | *V. rupestris* × *M. rotundifolia* |
| '9363-16' | (*V. rufotomentosa* × (*V. champinii* 'Dog Ridge' × 'Riparia Gloire')) × *'Riparia Gloire'* |
| '9365-43' | (*V. rufotomentosa* × (*V. champinii* 'Dog Ridge' × 'Riparia Gloire')) × *V. champinii 'c9038' (probably V. candicans* × *V. monticola*) |
| '9365-85' | (*V. rufotomentosa* × (*V. champinii* 'Dog Ridge' × 'Riparia Gloire')) × *V. champinii* 'c9038' (probably *V. candicans* × *V. monticola*) |
| '9407-14' | (*V. champinii* 'Ramsey' × 'Riparia Gloire')) × *V. champinii* 'c9021' (probably *V. candicans* × *V. berlandieri*) |

TABLE 2

Selections with broad resistance to four nematodes when inoculated individually.

| Selection | X. index | M. incognita I3 | M. arenaria-HarmA | M. incognita-HarmC |
|---|---|---|---|---|
| '8909-05' | R | R | R | R |
| '9317-06' | R | R | R | R |
| '9332-43' | R | R | R | R |
| '9344-03' | R | R | R | R |
| '9363-16' | R | R | R | R |
| '9365-43' | R | R | R | R- |
| '9365-62' | R | R | R | R |
| '9365-85' | R- | R | R | R |
| '9403-35' | R | R | R- | R- |

TABLE 2-continued

Selections with broad resistance to four nematodes when inoculated individually.

| Selection | X. index | M. incognita I3 | M. arenaria-HarmA | M. incognita-HarmC |
|---|---|---|---|---|
| '9403-107' | R | R | R | R |
| '9407-14' | R | R | R | R |
| '9449-23' | R | R | R | R |
| '9449-25' | R | R | R | R |
| '9449-27' | R | R | R | R |
| Control Group: | | | | |
| '1616C' | S | R | R- | R- |
| 'Harmony' | S | R | S | S |
| 'Colombard' | S | S | S | S |

R = Resistant, no gall symptoms or egg masses observed

R- = Trace infection

S = Susceptible, symptoms present, nematode reproduction supported

TABLE 3

Summary results for 14 nematode resistant selections when tested against combined inoculum with three root-knot nematode (RKN) strains and dagger nematode (Xi). Results of testing against citrus, lesion and ring are also reported.

| Genotypes | Xi Galls in Combined Testing | | RKN Egg Masses in Combined Testing | |
|---|---|---|---|---|
| '8909-05' | R | 0 | R | 0 |
| '9317-06' | MS | <1 | S | <5 |
| '9332-43' | S | <5 | S | <5 |
| '9344-03' | S | <5 | MS | <1 |
| '9363-16' | R | 0 | R | 0 |
| '9365-43' | R | 0 | R- | <1 |
| '9365-62' | MS | <1 | S | <5 |
| '9365-85' | MS | <1 | R- | <1 |
| '9403-107' | R | 0 | S | <5 |
| '9403-35' | S | <5 | S | <5 |
| '9407-14' | R | 0 | R | 0 |
| '9449-23' | MS | <1 | R | 0 |
| '9449-25' | MS | <1 | R | 0 |
| '9449-27' | MS | <1 | R- | <1 |
| '1616C' | S | >50 | S | <5 |
| 'Freedom' | S | >10 | S | <10 |
| 'Colombard' | S | >100 | S | >100 |
| 'Harmony' | S | >10 | S | <50 |
| 'St. George' | S | >100 | S | <50 |

| Genotypes | Citrus | | Lesion | | Ring | |
|---|---|---|---|---|---|---|
| '8909-05' | R | <100 | R | <10 | R | <1,000 |
| '9317-06' | R | <100 | R | <50 | HS | <20,000 |
| '9332-43' | R | <100 | R | <50 | S | <10,000 |
| '9344-03' | S | >400 | S | <200 | S | <10,000 |
| '9363-16' | S | >400 | R | <50 | S | <10,000 |
| '9365-43' | R | <100 | R | <50 | MS | <5,000 |
| '9365-62' | R | <100 | R | <50 | MS | <5,000 |
| '9365-85' | R | <100 | R | <50 | S | <10,000 |
| '9403-107' | R | <100 | R | <50 | MS | <5,000 |
| '9403-35' | | | R | <50 | MS | <5,000 |
| '9407-14' | R | <100 | R | <50 | LS | <3,000 |
| '9449-23' | R | <100 | R | <50 | S | <10,000 |
| '9449-25' | R | <100 | R | <50 | S | <10,000 |
| '9449-27' | R | <100 | R | <50 | S | <10,000 |
| '1616C' | S | >400 | S | <200 | HS | <20,000 |
| 'Freedom' | R | <100 | R | <50 | HS | <20,000 |
| 'Colombard' | S | <1000 | S | <300 | HS | <30,000 |
| 'Harmony' | S | <1000 | S | <200 | HS | <30,000 |
| 'St. George' | S | >400 | R | <50 | S | <10,000 |

TABLE 4

Number of egg masses per potted plant and per gram of root after inoculation with 1,000 M. arenaria 'HarmA' nematodes and testing at 32 C.

| Genotype | Egg Mass/Plant | Egg Mass/g Root |
|---|---|---|
| 'Colombard' | 442.50 a | 155.86 a |
| 'Harmony' | 156.00 b | 123.28 b |
| '9365-85' | 32.25 c | 16.49 c |
| '9365-43' | 7.25 c | 6.04 cd |
| '9363-16' | 6.75 c | 5.74 cd |
| '9449-27' | 0.25 c | 0.22 d |
| '9317-06' | 0.00 c | 0 d |
| '8909-05' | 0.00 c | 0 d |

TABLE 5

The average rate of population increase of phylloxera on nodosities formed on young root tips of advanced rootstock selections and a set of standard rootstocks. The phylloxera were selected from a vineyard planted on '101-14 Mgt' rootstock.

| | |
|---|---|
| '8909-05' | 0.59 |
| '9363-16' | 0.89 |
| '9365-43' | 1.86 |
| '9365-85' | 1.99 |
| '9407-14' | 9.83 |
| '9449-27' | 0.30 |
| '1103P' | 2.10 |
| '101-14 Mgt' | 7.98 |
| 'Teleki 5C' | 1.38 |

TABLE 5-continued

The average rate of population increase of phylloxera on nodosities formed on young root tips of advanced rootstock selections and a set of standard rootstocks. The phylloxera were selected from a vineyard planted on '101-14 Mgt' rootstock.

| | |
|---|---|
| 'AxR#1' | 2.15 |
| 'O39-16' | 0.43 |

TABLE 6

Number of root-knot nematode egg masses recovered from rootstock selections growing in 1 gal pots with soils collected from sites at the Gallo Livingston vineyards. this vineyard is known to have severe and chronic nematode pressure. Results per soils are means of three replicate pots.

| Selection | Soil 1 | Soil 2 | Soil 3 |
|---|---|---|---|
| 'Colombard' | 69.02 | 89.8 | 74.6 |
| 'Harmony' | 31.2 | 0 | 2.8 |
| 'St. George' | 9.8 | 26.2 | 16.0 |
| '9365-85' | 1 | 0 | 1.4 |
| '9407-14' | 0 | 0 | 0 |
| '9363-16' | 0 | 0 | 1.4 |
| '9365-43' | 0 | 0 | 0.2 |
| '9449-27' | 0 | 0 | 0.8 |
| '8909-05' | 0 | 0 | 0 |

What is claimed is:

1. A novel and distinct variety of grape rootstock designated '9365-43' having the characteristics described and illustrated herein.

* * * * *